(12) United States Patent
Muslet et al.

(10) Patent No.: US 9,327,477 B2
(45) Date of Patent: May 3, 2016

(54) ELASTOMERIC MATERIALS (75) Inventors: Iyad Muslet, West Chester, OH (US);
David G. Bland, Vero Beach, FL (US);
Leopoldo V. Cancio, Vero Beach, FL
(US); Jean-Philippe Marie Autran,
Wyoming, OH (US)

(73) Assignee: Clopay Plastic Products Company, Inc., Mason, OH (US)

( * ) Notice: Subject to any disclaimer, the term of this patent is extended or adjusted under 35 U.S.C. 154(b) by 743 days.

(21) Appl. No.: 12/358,533

(22) Filed: Jan. 23, 2009

(65) Prior Publication Data

US 2009/0258210 A1 Oct. 15, 2009

Related U.S. Application Data

(60) Provisional application No. 61/023,107, filed on Jan. 24, 2008.

(51) Int. Cl.
*B32B 27/32* (2006.01)
*A61F 13/15* (2006.01)
(Continued)

(52) U.S. Cl.
CPC ............ *B32B 27/32* (2013.01); *A61F 13/15593* (2013.01); *A61F 13/4902* (2013.01); *B32B 25/08* (2013.01); *B32B 25/10* (2013.01); *B32B 25/16* (2013.01); *B32B 27/12* (2013.01); *B32B 27/30* (2013.01); *C08L 23/0815* (2013.01); *C08L 23/142* (2013.01); *C08L 23/16* (2013.01); *C08L 53/00* (2013.01); *C08L 53/02* (2013.01); *C08L 53/025* (2013.01); *B32B 2270/00* (2013.01); *B32B 2307/51* (2013.01); *B32B 2555/00* (2013.01); *B32B 2555/02* (2013.01); *C08L 23/06* (2013.01); *C08L 23/12* (2013.01);
(Continued)

(58) Field of Classification Search
CPC ........ B32B 25/08; B32B 25/10; B32B 25/12; B32B 25/16; B32B 27/12; B32B 27/30; B32B 27/32; B32B 2555/02; Y10T 428/273; Y10T 428/24942
USPC ..................... 442/394, 398; 428/98
See application file for complete search history.

(56) References Cited

U.S. PATENT DOCUMENTS 3,914,488 A * 10/1975 Gorrafa ...................... 428/397
4,527,990 A 7/1985 Sigl
(Continued)

FOREIGN PATENT DOCUMENTS

JP 62-131044 A 6/1987
JP 4-185660 A 7/1992
(Continued)

OTHER PUBLICATIONS

International Search Report and Written Opinion, Application No. PCT/US2009/031779, mailed May 7, 2009, 15 pp.
(Continued)

*Primary Examiner* — Jeremy R Pierce
(74) *Attorney, Agent, or Firm* — Wood, Herron & Evans, LLP (57) ABSTRACT

Some embodiments of the present invention include elastomeric films with a basis weight of about 40 gsm or less or about 25 gsm or less. Other embodiments include elastomeric laminates comprising the elastomeric film bonded to one or more substrates (such as nonwoven fabrics). Methods of the making the elastomeric films and elastomeric laminates are also provided.

29 Claims, 3 Drawing Sheets

(51) Int. Cl.
  *A61F 13/49* (2006.01)
  *B32B 25/08* (2006.01)
  *B32B 25/10* (2006.01)
  *B32B 25/16* (2006.01)
  *B32B 27/12* (2006.01)
  *B32B 27/30* (2006.01)
  *C08L 23/08* (2006.01)
  *C08L 23/14* (2006.01)
  *C08L 23/16* (2006.01)
  *C08L 53/00* (2006.01)
  *C08L 53/02* (2006.01)
  *C08L 23/06* (2006.01)
  *C08L 23/12* (2006.01)

(52) U.S. Cl.
  CPC ..... *C08L 2205/02* (2013.01); *Y10T 428/24942* (2015.01); *Y10T 428/273* (2015.01)

(56) References Cited

U.S. PATENT DOCUMENTS

| | | | |
|---|---|---|---|
| 4,863,779 | A | 9/1989 | Daponte |
| 4,908,263 | A | 3/1990 | Reed et al. |
| 4,929,492 | A | 5/1990 | Carey, Jr. et al. |
| 4,935,287 | A | 6/1990 | Johnson et al. |
| 4,965,122 | A | 10/1990 | Morman |
| 4,981,747 | A | 1/1991 | Morman |
| 5,075,142 | A | 12/1991 | Zafiroglu |
| 5,075,143 | A | 12/1991 | Bekele |
| 5,112,690 | A | 5/1992 | Cohen et al. |
| 5,114,781 | A | 5/1992 | Morman |
| 5,116,662 | A | 5/1992 | Morman |
| 5,209,801 | A | 5/1993 | Smith |
| 5,260,123 | A | 11/1993 | Hergenrother et al. |
| 5,302,443 | A | 4/1994 | Manning et al. |
| 5,308,906 | A | 5/1994 | Taylor et al. |
| 5,316,838 | A | 5/1994 | Crandall et al. |
| 5,332,613 | A | 7/1994 | Taylor et al. |
| 5,336,545 | A | 8/1994 | Morman |
| 5,344,691 | A | 9/1994 | Hanschen et al. |
| 5,376,430 | A | 12/1994 | Swenson et al. |
| 5,385,755 | A | 1/1995 | Staley |
| 5,385,972 | A | 1/1995 | Yamamoto et al. |
| 5,393,599 | A | 2/1995 | Quantrille et al. |
| 5,422,172 | A | 6/1995 | Wu |
| 5,468,428 | A | 11/1995 | Hanschen et al. |
| 5,492,753 | A | 2/1996 | Levy et al. |
| 5,501,679 | A | 3/1996 | Krueger et al. |
| 5,514,470 | A | 5/1996 | Haffner et al. |
| 5,529,830 | A | 6/1996 | Dutta et al. |
| 5,540,976 | A | 7/1996 | Shawver et al. |
| 5,576,090 | A | 11/1996 | Suzuki |
| 5,634,216 | A | 6/1997 | Wu |
| 5,635,275 | A | 6/1997 | Biagioli et al. |
| 5,635,276 | A | 6/1997 | Biagioli et al. |
| 5,635,290 | A | 6/1997 | Stopper et al. |
| 5,652,051 | A | 7/1997 | Shawver et al. |
| 5,680,653 | A | 10/1997 | Mathis et al. |
| 5,683,787 | A | 11/1997 | Boich et al. |
| 5,695,849 | A | 12/1997 | Shawver et al. |
| 5,695,868 | A | 12/1997 | McCormack |
| 5,709,921 | A | 1/1998 | Shawver |
| 5,733,628 | A | 3/1998 | Pelkie |
| 5,733,822 | A | 3/1998 | Gessner et al. |
| 5,773,374 | A | 6/1998 | Wood et al. |
| 5,789,065 | A | 8/1998 | Haffner et al. |
| 5,804,021 | A | 9/1998 | Abuto et al. |
| 5,807,368 | A | 9/1998 | Helmer |
| 5,814,390 | A | 9/1998 | Stokes et al. |
| 5,814,569 | A | 9/1998 | Suzuki et al. |
| 5,827,252 | A | 10/1998 | Werenicz et al. |
| 5,830,555 | A | 11/1998 | Srinivasan et al. |
| 5,840,412 | A | 11/1998 | Wood et al. |
| 5,843,057 | A | 12/1998 | McCormack |
| 5,851,935 | A | 12/1998 | Srinivasan et al. |
| 5,851,937 | A | 12/1998 | Wu et al. |
| 5,853,881 | A | 12/1998 | Estey et al. |
| 5,883,028 | A | 3/1999 | Morman et al. |
| 5,885,908 | A | 3/1999 | Jaeger et al. |
| 5,910,224 | A | 6/1999 | Morman |
| 5,921,973 | A | 7/1999 | Newkirk et al. |
| 5,938,648 | A | 8/1999 | LaVon et al. |
| 5,939,178 | A | 8/1999 | Boich |
| 5,942,080 | A | 8/1999 | Mortellite et al. |
| 5,952,252 | A | 9/1999 | Shawver et al. |
| 6,001,460 | A | 12/1999 | Morman et al. |
| 6,028,017 | A | 2/2000 | Curtin et al. |
| 6,042,882 | A | 3/2000 | Deeb et al. |
| 6,045,900 | A | 4/2000 | Haffner et al. |
| 6,069,097 | A | 5/2000 | Suzuki et al. |
| 6,093,496 | A | 7/2000 | Dominguez et al. |
| 6,096,668 | A | 8/2000 | Abuto et al. |
| 6,106,925 | A | 8/2000 | Palumbo |
| 6,117,523 | A | 9/2000 | Sugahara |
| 6,120,887 | A | 9/2000 | Werenicz et al. |
| 6,159,584 | A | 12/2000 | Eaton et al. |
| 6,197,404 | B1 | 3/2001 | Varona |
| 6,198,018 | B1 | 3/2001 | Curro |
| 6,214,147 | B1 | 4/2001 | Mortellite et al. |
| 6,238,767 | B1 | 5/2001 | McCormack et al. |
| 6,245,401 | B1 | 6/2001 | Ying et al. |
| 6,303,208 | B1 | 10/2001 | Pelkie |
| 6,313,372 | B1 | 11/2001 | Suzuki |
| 6,316,688 | B1 | 11/2001 | Hammons et al. |
| 6,383,431 | B1 | 5/2002 | Dobrin et al. |
| 6,387,471 | B1 | 5/2002 | Taylor et al. |
| 6,410,129 | B2 | 6/2002 | Zhang et al. |
| 6,410,465 | B1* | 6/2002 | Lim et al. ...................... 442/389 |
| 6,420,049 | B1 | 7/2002 | Restaino et al. |
| 6,436,080 | B1 | 8/2002 | Carlucci et al. |
| 6,461,339 | B1 | 10/2002 | Sugahara |
| 6,461,457 | B1 | 10/2002 | Taylor et al. |
| 6,463,606 | B2 | 10/2002 | Barker et al. |
| 6,464,106 | B1 | 10/2002 | Giblin et al. |
| 6,465,073 | B1 | 10/2002 | Morman et al. |
| 6,472,084 | B1 | 10/2002 | Middlesworth et al. |
| 6,475,600 | B1 | 11/2002 | Morman et al. |
| 6,475,932 | B1 | 11/2002 | Stuczynski et al. |
| 6,476,289 | B1 | 11/2002 | Buell et al. |
| 6,479,154 | B1 | 11/2002 | Walton et al. |
| 6,500,563 | B1* | 12/2002 | Datta et al. ................... 428/521 |
| 6,503,855 | B1 | 1/2003 | Menzies et al. |
| 6,506,695 | B2 | 1/2003 | Gardner et al. |
| 6,537,930 | B1 | 3/2003 | Middlesworth et al. |
| 6,547,915 | B2 | 4/2003 | Taylor et al. |
| 6,551,436 | B1 | 4/2003 | Flohr et al. |
| 6,572,976 | B1 | 6/2003 | Puckett et al. |
| 6,582,810 | B2 | 6/2003 | Heffelfinger |
| 6,583,332 | B1 | 6/2003 | Werenicz et al. |
| 6,605,552 | B2 | 8/2003 | Jackson et al. |
| 6,617,016 | B2 | 9/2003 | Zhang et al. |
| 6,623,586 | B2 | 9/2003 | Mortellite et al. |
| 6,623,837 | B2 | 9/2003 | Morman et al. |
| 6,627,564 | B1 | 9/2003 | Morman et al. |
| 6,649,546 | B2 | 11/2003 | Ohata |
| 6,653,523 | B1 | 11/2003 | McCormack et al. |
| 6,677,258 | B2 | 1/2004 | Carroll et al. |
| 6,680,265 | B1 | 1/2004 | Smith et al. |
| 6,682,512 | B2 | 1/2004 | Uitenbroek et al. |
| 6,682,514 | B1 | 1/2004 | Brunner |
| 6,713,159 | B2 | 3/2004 | Blenke et al. |
| 6,720,063 | B2 | 4/2004 | Kobayashi et al. |
| 6,726,983 | B2 | 4/2004 | Erdos et al. |
| 6,730,390 | B1 | 5/2004 | Kobayashi et al. |
| 6,733,484 | B2 | 5/2004 | Van Gompel et al. |
| 6,750,161 | B2 | 6/2004 | Putnam et al. |
| 6,794,024 | B1 | 9/2004 | Walton et al. |
| 6,808,789 | B2 | 10/2004 | Pelkie et al. |
| 6,808,790 | B2 | 10/2004 | Chen et al. |
| 6,811,643 | B2 | 11/2004 | McAmish et al. |
| 6,818,083 | B2 | 11/2004 | McAmish et al. |
| 6,821,610 | B2 | 11/2004 | Hamulski et al. |
| 6,830,800 | B2 | 12/2004 | Curro et al. |

(56) References Cited

U.S. PATENT DOCUMENTS

| | | |
|---|---|---|
| 6,835,256 B2 | 12/2004 | Menzies et al. |
| 6,843,872 B2 | 1/2005 | Morman |
| 6,843,874 B1 | 1/2005 | Janssen |
| 6,849,319 B2 | 2/2005 | Cree et al. |
| 6,849,324 B2 | 2/2005 | Meece et al. |
| 6,852,392 B2 | 2/2005 | Kikuchi et al. |
| 6,855,223 B2 | 2/2005 | Johnson |
| 6,855,424 B1 | 2/2005 | Thomas et al. |
| 6,902,796 B2 | 6/2005 | Morell et al. |
| 6,909,028 B1 | 6/2005 | Shawver et al. |
| 6,914,018 B1 | 7/2005 | Uitenbroek et al. |
| 6,916,750 B2 | 7/2005 | Thomas et al. |
| 6,938,309 B2 | 9/2005 | Gorman et al. |
| 6,939,334 B2 | 9/2005 | Odorzynski et al. |
| 6,942,748 B2 | 9/2005 | Cree et al. |
| 6,951,591 B2 | 10/2005 | Mortellite et al. |
| 6,953,510 B1 | 10/2005 | Mackay et al. |
| 6,960,375 B2 | 11/2005 | Giblin et al. |
| 6,964,720 B2 | 11/2005 | Schneider et al. |
| 6,967,178 B2 | 11/2005 | Zhou et al. |
| 6,969,378 B1 | 11/2005 | Vukos et al. |
| 6,972,010 B2 | 12/2005 | Pesce et al. |
| 6,974,514 B2 | 12/2005 | Hamulski et al. |
| 6,978,486 B2 | 12/2005 | Zhou et al. |
| 6,982,231 B1 | 1/2006 | Uitenbroek et al. |
| 6,994,763 B2 | 2/2006 | Austin |
| 7,005,558 B1 | 2/2006 | Johansson et al. |
| 7,014,631 B2 | 3/2006 | Jackson et al. |
| 7,024,939 B2 | 4/2006 | Anderson et al. |
| 7,037,569 B2 | 5/2006 | Curro et al. |
| 7,039,990 B2 | 5/2006 | Gorman et al. |
| 7,074,215 B2 | 7/2006 | Ashton et al. |
| 7,078,075 B1 | 7/2006 | Werenicz et al. |
| 7,078,089 B2 | 7/2006 | Ellis et al. |
| 7,083,691 B2 | 8/2006 | Hamulski et al. |
| 7,087,285 B2 | 8/2006 | Zafiroglu |
| 7,087,287 B2 | 8/2006 | Curro et al. |
| 7,118,639 B2 | 10/2006 | DeLucia et al. |
| 7,189,448 B2 | 3/2007 | Raidel et al. |
| 7,198,742 B2 | 4/2007 | Gerndt |
| 7,204,907 B2 | 4/2007 | Cree et al. |
| 7,211,531 B2 | 5/2007 | Schneider |
| 7,220,478 B2 | 5/2007 | McCormack et al. |
| 7,247,675 B2 | 7/2007 | Thomas et al. |
| 7,300,426 B2 | 11/2007 | Jackson |
| 7,303,642 B2 | 12/2007 | Topolkaraev |
| 7,307,031 B2 | 12/2007 | Carroll et al. |
| 7,316,840 B2 | 1/2008 | Neculescu et al. |
| 7,316,842 B2 | 1/2008 | Zhou et al. |
| 7,320,948 B2 | 1/2008 | Morman et al. |
| 7,326,751 B2 | 2/2008 | DeLucia et al. |
| 7,329,621 B2 | 2/2008 | Collier, IV et al. |
| 7,335,273 B2 | 2/2008 | Neculescu et al. |
| 7,335,423 B2 | 2/2008 | Huber |
| 7,338,625 B2 | 3/2008 | Kellenberger et al. |
| 7,341,084 B2 | 3/2008 | Van Eperen |
| 7,355,091 B2 | 4/2008 | Kellenberger et al. |
| 7,410,683 B2 | 8/2008 | Curro et al. |
| 2003/0181120 A1* | 9/2003 | Wu et al. ........................ 442/394 |
| 2005/0215963 A1 | 9/2005 | Autran et al. |
| 2005/0215964 A1 | 9/2005 | Autran et al. |
| 2006/0199457 A1* | 9/2006 | Hall et al. ...................... 442/399 |
| 2006/0216473 A1 | 9/2006 | Tomany et al. |
| 2006/0257666 A1 | 11/2006 | Muslet |
| 2007/0003764 A1 | 1/2007 | Muslet et al. |
| 2007/0155900 A1* | 7/2007 | Chang et al. ..................... 525/88 |
| 2007/0287348 A1 | 12/2007 | Autran et al. |
| 2008/0207071 A1 | 8/2008 | Muslet et al. |

FOREIGN PATENT DOCUMENTS

| | | |
|---|---|---|
| JP | 09-067453 A | 3/1997 |
| JP | 2004-050621 A | 2/2004 |
| WO | 2005/103141 A | 11/2005 |
| WO | 2007001619 A1 | 1/2007 |
| WO | 2007141745 A2 | 12/2007 |
| WO | 2007146148 A2 | 12/2007 |
| WO | 2007146149 A2 | 12/2007 |
| WO | 2007146153 A2 | 12/2007 |

OTHER PUBLICATIONS

Egyptian Official Action issued in Egyptian Patent Applicatino No. 1234/2010, dated Nov. 10, 2011, 3 pages.

Israeli Official Action issued in Israeli Patent Application No. 207101, dated Oct. 27, 2011, 1 page.

Eurasian Official Action issued in Eurasian Patent Application No. 201070879, Dec. 23, 2011, 2 pages.

New Zealand Examination Report issued in New Zealand Patent Application No. 586914, dated Feb. 18, 2011, 2 pages.

European Official Action issued in European Patent Application No. 09703318.7, dated Feb. 28, 2011, 7 pages.

European Official Action issued in European Patent Application No. 09703318.7, dated Jan. 17, 2012, 5 pages.

Extended European Search Report issued in corresponding European Application No. 13155905.6 mailed on Jun. 7, 2013 (5 pages).

Notice of Reasons for Rejection issued in Japanese Patent Application No. 2010-544430; Feb. 5, 2013; 4 pages.

Translation of letter from Andrejewski dated Jun. 30, 2015 re Opposition of EP 2 242 465 (8 pages).

\* cited by examiner

ELASTOMERIC MATERIALS

CROSS REFERENCE TO RELATED APPLICATION

This application claims the benefit of U.S. Provisional Application No. 61/023,107, filed Jan. 24, 2008, which is herein incorporated by reference in its entirety.

BACKGROUND

Elastomeric materials have the ability to expand to fit over or around an object, and then retract to provide a snug fit around the object. Elastomeric materials can be used in garments to provide a snug fit, such as in active wear. Elastomeric materials can also form resilient and effective barriers, such as in the cuffs of thermal garments intended to retain body heat.

One example of a type of garment where both fit and barrier properties are important is personal hygienic products such as diapers. Elastomeric materials can be used in the waist, around the leg openings, and in the fasteners (for a diaper) or sides (for an underpants-type garment). The elastomeric materials in these regions can improve the overall fit of the garment, and also make it much easier to both don and remove the garment. The elastomeric materials also act as resilient barriers, improving the containment capabilities of the garment while still allowing comfort and free movement to the wearer.

Elastomeric materials can be expensive and producing thin films of expensive material can therefore reduce cost. However, producing thin films can be complicated due to tearing and pinholing.

There remains a need for an inexpensive elastomeric film, or an inexpensive laminate of an elastomeric film that is bonded to one or more layers of substrate, such as fabric. There also remains a need for an elastomeric film or laminate that has good elastomeric properties, such as permanent set. Such a film or laminate can be suitable for improving the fit and comfort of garments and personal care items, including limited-use and disposable items.

SUMMARY

Some embodiments of the present invention relate to an elastomeric film comprising a layer comprising (i) at least one olefin-based elastomeric polymer, and (ii) at least one draw down polymer. The elastomeric film has a basis weight of no more than about 25 gsm and has a permanent set of no more than about 15% after recovery from being stretched to 100% of its original size.

Other embodiments include a multilayer elastomeric film with two or more layers comprising (1) a first layer comprising (a) at least one olefin-based elastomeric polymer and (b) at least one first draw down polymer, and (2) a second layer comprising (a) at least one elastomeric polymer and (b) at least one second draw down polymer. The multilayer elastomeric film has a basis weight of no more than about 40 gsm and has a permanent set of no more than about 15% after recovery from being stretched to 100% of its original size. And at least one elastomeric polymer of the second layer can be an olefin-based elastomeric polymer, a non-olefin-based elastomeric polymer, or combinations thereof.

Other embodiments include a multilayer elastomeric film that further comprises a third layer comprising at least one second elastomeric polymer and at least one third draw down polymer.

Some embodiments of the invention include a laminate comprising a film that can be a monolayer elastomeric film or a multilayer elastomeric film and at least one substrate. The film and the substrate are laminated together to form the laminate.

Further embodiments include a method for making an elastomeric film comprising extruding a mixture into a layer of a film. The mixture comprises at least one olefin-based elastomeric polymer and at least one draw down polymer.

Some embodiments include a method for making a multilayer elastomeric film with at least two layers comprising coextruding a first layer and a second layer. The first layer comprises at least one olefin-based elastomeric polymer and at least one first draw down polymer. The second layer comprises at least one elastomeric polymer and at least one second draw down polymer.

Other embodiments include a method for making a multilayer elastomeric film with at least three layers comprising coextruding a first layer, a second layer, and a third layer. The first layer comprises at least one olefin-based elastomeric polymer and at least one first draw down polymer. The second layer comprises at least one elastomeric polymer and at least one second draw down polymer. The third layer comprises at least one second elastomeric polymer and at least one third draw down polymer.

Some embodiments include a method for making a laminate comprising laminating a film to at least one substrate. The film is an elastomeric film or a multilayer elastomeric film.

BRIEF DESCRIPTION OF THE DRAWINGS

The invention will be more fully understood in view of the drawings, in which.

DETAILED DESCRIPTION

For the purpose of this disclosure, the following terms are defined:

"Film" refers to material in a sheet-like form where the dimensions of the material in the x (length) and y (width) directions are substantially larger than the dimension in the z (thickness) direction.

"Basis weight" is an industry standard term that quantifies the thickness or unit mass of a film or laminate product. The basis weight is the mass per planar area of the sheet-like material. Basis weight is commonly stated in units of grams per square meter (gsm) or ounces per square yard (osy).

"Coextrusion" refers to a process of making multilayer polymer films. When a multilayer polymer film is made by a coextrusion process, each polymer or polymer blend comprising a layer of the film is melted by itself. The molten polymers may be layered inside the extrusion die, and the layers of molten polymer films are extruded from the die essentially simultaneously. In coextruded polymer films, the individual layers of the film are bonded together but remain essentially unmixed and distinct as layers within the film. This is contrasted with blended multicomponent films, where the polymer components are mixed to make an essentially homogeneous blend or heterogeneous mixture of polymers that are extruded in a single layer.

"Laminate" as a noun refers to a layered structure of sheet-like materials stacked and bonded so that the layers are substantially coextensive across the width of the narrowest sheet of material. The layers may comprise films, fabrics, other materials in sheet form, or combinations thereof. For instance, a laminate may be a structure comprising a layer of film and a layer of fabric bonded together across their width such that the two layers remain bonded as a single sheet under normal use. A laminate may also be called a composite or a coated material. "Laminate" as a verb refers to the process by which such a layered structure is formed.

"Extrusion lamination" or "extrusion coating" refer to processes by which a film of molten polymer is extruded onto a solid substrate, in order to coat the substrate with the molten polymer film to bond the substrate and film together.

"Elastomeric" or "elastomer" refer to polymer materials which can be stretched to at least about 150% or more of their original dimension, and which then recover to no more than about 120% of their original dimension in the direction of the applied stretching force. For example, an elastomeric film that is 10 cm long should stretch to at least about 15 cm under a suitable stretching force, and then retract to no more than about 12 cm when the stretching force is removed. Elastomeric materials are both stretchable and recoverable.

"Permanent set" is the permanent deformation of a material after removal of an applied load. In the case of elastomeric films, permanent set is the increase in length of a sample of a film after the film has been stretched to a given length and then allowed to relax. Permanent set is typically expressed as a percent increase relative to the original size. For example, if a 10 cm piece of elastomeric film is stretched to 20 cm, then allowed to relax, and the resulting relaxed film is 11.5 cm in length, the permanent set of the film is 15%.

The test method used to measure permanent set is based upon ASTM D882-97 with the following details. The sample is cut to make one inch by six inch specimens—the six inch length is in the direction the of the film or laminate is being tested (e.g., in the CD direction for the examples below). An MTS Tensile Tester (Qtest) is used to measure the sample deformation. The tester grip faces are rubber grip faces that are 25 mm wide (MTS part No. 56163829). The sample is loaded with a grip distance set at two inches from the center of upper grip face to the center of the lower grip face. The strain endpoint is set to 100%. The first upload cycle is run at a rate of 20 inches/minute to the strain endpoint, then immediately returns to 0% strain at a rate of 20 inches/minute, and then is held at 0% strain for 30 seconds. The second upload cycle is run at a rate of 20 inches/minute to the strain endpoint, and then immediately returns to 0% strain at a rate of 20 inches/minute. The permanent set is calculated at the point when load reaches eight grams of force during the second upload cycle.

"Stretchable" and "recoverable" are descriptive terms used to describe the elastomeric properties of a material. "Stretchable" means that the material can be extended by a pulling force to a specified dimension significantly greater than its initial dimension without breaking. For example, a material that is 10 cm long that can be extended to about 13 cm long without breaking under a pulling force could be described as stretchable. "Recoverable" means that a material which is extended by a pulling force to a certain dimension significantly greater than its initial dimension without breaking will return to its initial dimension or a specified dimension that is adequately close to the initial dimension when the pulling force is released. For example, a material that is 10 cm long that can be extended to about 13 cm long without breaking under a pulling force, and which returns to about 10 cm long or to a specified length that is adequately close to 10 cm could be described as recoverable.

"Extensible" refers to polymer materials that can be stretched at least about 130% of their original dimension without breaking, but which either do not recover significantly or recover to greater than about 120% of their original dimension and therefore are not elastomeric as defined above. For example, an extensible film that is 10 cm long should stretch to at least about 13 cm under a stretching force, then either remain about 13 cm long or recover to a length more than about 12 cm when the stretching force is removed. Extensible materials are stretchable, but not recoverable.

"Activation" or "activating" refers to a process by which the elastomeric film or material is rendered easy to stretch. Most often, activation is a physical treatment, modification or deformation of the elastomeric film. Stretching a film for the first time is one means of activating the film. An elastomeric material that has undergone activation is called "activated." A common example of activation is blowing up a balloon. The first time the balloon is inflated (or "activated"), the material in the balloon is stretched. If the inflated balloon is allowed to deflate and then blown up again, the "activated" balloon is much easier to inflate.

"Film strength" or "mechanical strength" are the tensile properties of a film or laminate, as measured by ASTM D-822 "Tensile Properties of Thin Plastic Sheeting." Unless noted otherwise, "film strength" or "mechanical strength" refers specifically to tensile at break and % elongation at break.

"Tear strength" is a property of a film which determines the ease or difficulty by which the film can be torn starting from a notch or aperture cut into the film, as measured by the notched Elmendorf test, ASTM D-1922.

"Bond strength" is a property of a laminate comprising two or more layers. The bond strength is determined by measuring the force required to peel apart the laminate layers after they are bonded together. Bond strength can be measured by methods such as ASTM D-1876 or ASTM F-904.

"Pinholing" refers to the formation of small holes or tears in a film while the film is being formed, laminated, activated, or other manufacturing or processing step. "Pinholes" are the small holes or tears so formed. Pinholes are typically in the range of about 100 μm to 1 cm in size.

"Processability" is a catch-all term to qualitatively describe the ease with which a composition comprising a polymer resin or polymer resin blend can be extruded to form a film. If a polymer composition has good processability, it can be easily extruded into a uniform film with a smooth surface, controlled and uniform thickness, thinner gauge, homogeneous composition, etc. Poor processability is demonstrated by problems such as draw resonance, 'shark skin' surfaces, poor thickness control, inability to reduce the film gauge, etc.

"Blocking" refers to the phenomenon of a material sticking to itself while rolled, folded, or otherwise placed in intimate surface-to-surface contact, due to the inherent stickiness or tackiness of one or more of the material components. Blocking can be quantified by ASTM D3354 "Blocking Load of Plastic Film by the Parallel Plate Method."

"Robust" refers generally to the tendency of a film, laminate, or other sheet-like material to remain intact and resist tearing, shredding, pinholing, or other forms of material failure while under applied stress or other physical manipulation. For example, a film which resists tearing under a given stress is described as 'more robust' than another film which tears under equivalent stress.

According to the present invention, as discussed herein, an elastomeric film with a low basis weight can be produced. In some embodiments, the elastomeric film is a monolayer film of a polyolefin-based layer. The elastomeric film can also be a multilayer film having a polyolefin-based layer. The multilayer film can have a total of, for example, two layers, three layers, four layers, five layers, six layers, seven layers, or eight or more layers. The elastomeric film can also be part of a laminate formed with one or more substrates, such as nonwoven fabrics.

The monolayer elastomeric film comprises a polyolefin-based layer that comprises one or more olefin-based elastomeric polymers blended with one or more draw down polymers.

The draw down polymer is a polymer that adds or enhances one or more film properties or processing properties, such as those that aid in processability during film preparation. For example, the draw down polymer can aid in the production of reduced-gauge (i.e., thin) films. In some embodiments, the draw down polymer can aid in the film extrusion, such as by helping to provide an increased line speed or reduce draw resonance. Other possible processability benefits from the addition of the draw down polymer include improving the melt curtain stability, providing a smooth film surface, providing a lower viscosity of the polymer melt, providing better resistance to heat (e.g., increasing the film's heat capacity or thermal stability), providing resistance to tearing, providing resistance to pinhole formation, providing a controlled and uniform thickness, or providing a homogeneous composition. The draw down polymer can act as a processing aid that lubricates the die to reduce sticking (e.g., of elastomeric polymers) and flow resistance of the molten elastomeric resin. Of course, the addition of the draw down polymer can provide one or a combination of these aids to film extrusion or processability.

There are many examples of draw down polymers. For example, a linear low-density polyethylene (e.g., ELITE™ 5800 provided by Dow Chemical Corp. of Midland, Mich.) can be added to a layer of the film composition to lower the viscosity of the polymer melt and enhance the processability of the extruded film. High-impact polystyrene (HIPS) (e.g., STYRON™ 485 from Dow Chemical Corp. of Midland, Mich.; IneosNova 473D from IneosNova of Channahon, Ill.) can help control the film modulus, improve the toughness of the film, and reduce the overall cost of the elastomeric material. Polypropylene can improve the robustness of the elastomer and improve the films' resistance to pinholing and tearing. Homopolymer polypropylene (hPP) (e.g., INSPIRE™ D118 from Dow Chemical Corp. of Midland, Mich.; Polypropylene 3622 from Total Petrochemicals of Houston, Tex.) can be added to improve processability. hPP is a form of polypropylene which is highly crystalline and containing essentially 100% propylene monomer. In some embodiments, hPP is added to a layer comprising an elastomeric polymer (e.g., styrene block copolymers), as discussed below; the addition can result, in some instances, in a film that can be extruded at a thinner gauge, with improved gauge uniformity, or with reduced tendency to experience draw resonance during extrusion.

The draw down polymers can be linear low density polyethylene, propylene, homopolymer polypropylene, high impact polystyrene, and mixtures thereof. The draw down polymer can be a polymer which has been prepared using a single-site catalyst such as a metallocene catalyst and can be, for example, a polyolefin produced using a metallocene catalyst (e.g., ELITE™ 5800 provided by Dow Chemical Corp. of Midland, Mich.). The identity and amount of draw down polymer can depend on the other components in the layer (e.g., the identity of the olefin-based elastomeric polymer(s) in the layer), other components of the film or, if applicable, components of the laminate that comprises the film. The total amount of draw down polymer can be present in an amount effective to enhance one or more film properties that aid in processability during film preparation; for example, the total amount of draw down polymer can be present in an amount effective to provide a film gauge of about 25 gsm, about 20 gsm, about 15 gsm, or about 10 gsm. The total amount of draw down polymer (i.e., the combined amount of the one or more draw down polymer(s)) can be about 5%, about 10 wt %, about 15 wt %, about 20 wt %, about 25 wt %, about 30 wt %, about 35 wt %, about 40 wt %, or about 45 wt %. The wt % is relative to the layer weight (i.e., total weight of draw down polymer(s) divided by the total weight of the layer). In some instances the total amount of the draw down polymer is at least about 5 wt %, at least about 10 wt %, or at least about 15 wt %. The total amount of draw down polymer can be no more than about 20 wt %, no more than about 25 wt %, no more than about 30 wt %, no more than about 35 wt %, or no more than about 45 wt %.

The olefin-based elastomeric polymer can be olefin block copolymer, olefin random copolymer, ethylene copolymer, propylene copolymer, or mixtures thereof. In some embodiments, the olefin-based elastomeric polymer is not a block copolymer of vinyl arylene and conjugated diene, natural rubber, polyurethane rubber, polyester rubber, elastomeric polyamide, elastomeric polyether, polyisoprene, polyneoprene, or mixtures thereof. In some embodiments, olefin-based elastomeric polymer can be ethylene olefin block copolymer, propylene olefin block copolymer, ethylene olefin random copolymer, propylene olefin random copolymer, or mixtures thereof. In other embodiments, the olefin-based elastomeric polymer can be ethylene-propylene random copolymer, ethylene-butene random copolymer, ethylene-pentene olefin block copolymer, ethylene-hexene random copolymer, ethylene-heptene olefin block copolymer, ethylene-octene olefin block copolymer, ethylene-nonene olefin block copolymer, ethylene-decene olefin block copolymer, propylene-ethylene olefin block copolymer, ethylene α-olefin copolymer, ethylene α-olefin random copolymer, ethylene α-olefin block copolymer, or mixtures thereof. Examples of olefin-based elastomeric polymers are olefin block copolymers (OBCs) which are elastomeric copolymers of polyethylene, sold under the trade name INFUSE™ by The Dow Chemical Company of Midland, Mich. (e.g., INFUSE™ 9107). Other examples of olefin-based elastomeric polymers are copolymers of polypropylene and polyethylene, sold under the trade name VISTAMAXX™ by ExxonMobil Chemical Company of Houston, Tex. (e.g., VISTAMAXX™ 6102). The total amount of the olefin-based elastomeric polymer(s) can be, relative to the layer weight, about 10 wt %, about 20 wt %, about 30 wt %, about 40 wt %, about 50 wt %, about 60 wt %, about 70 wt %, about 80 wt %, or about 90 wt %. In some instances, total amount of the olefin-based elastomeric polymer(s) can be at least about 10 wt %, at least about 20 wt %, at least about 50 wt %, or at least about 70 wt %. The total amount of the olefin-based elastomeric polymer(s) can be no more than about 70 wt %, no more than about 80 wt %, or no more than about 90 wt %.

The olefin-based elastomeric polymer can be present in an amount to provide or enhance properties (including processing properties) of the olefin-based layer or of the elastomeric film. The olefin-based elastomeric polymer can provide better resistance to heat (e.g., increasing the film's heat capacity or thermal stability), compared to, for example, unsaturated styrene block copolymer elastomers. This better resistance to heat can aid in processing or extrusion; for example, a film comprising olefin-based elastomeric polymers can make it possible to extrude at higher temperatures without significant thermal degradation, at lower viscosity, at a thinner gauge without tearing or pinholing, or combinations thereof. Olefin-based elastomeric polymers can have other enhanced processability characteristics (e.g., like some nonelastomeric polyolefins), and therefore they can be easier to extrude as thin films. Also, the olefin-based elastomeric polymers tend to be chemically similar to the polyolefins used for nonwovens. This chemical similarity can improve the chemical affinity between the film layer and nonwoven layer(s) in the laminate. Hence, the laminate can have improved bond strength due to chemical adhesion (e.g., via the chemical similarity) in addition to mechanical bonding.

Optionally, the polyolefin-based layer can include a non-olefin-based elastomeric polymer, which is blended with the one or more olefin-based elastomeric polymers and one or more draw down polymers.

A nonolefin-based elastomeric polymer can be, for example, block copolymer of vinyl arylene and conjugated diene, natural rubber, polyurethane rubber, polyester rubber, elastomeric polyamide, elastomeric polyether, polyisoprene, polyneoprene, or mixtures thereof. For instance, one group of nonolefin-based elastomeric polymers is the block copolymers of vinyl arylene and conjugated diene monomers, such as AB, ABA, ABC, or ABCA block copolymers where the A segments comprise arylenes such as polystyrene and the B and C segments comprise dienes such as butadiene or isoprene. Another group of nonolefin-based elastomeric polymers is the block copolymers of vinyl arylene and hydrogenated olefin monomers, such as AB, ABA, ABC, or ABCA block copolymers where the A segments comprise arylenes such as polystyrene and the B and C segments comprise saturated olefins such as ethylene, propylene, or butylene. A nonolefin-based elastomeric polymer can be styrene block copolymer (SBC), including but not limited to, styrene-butadiene-styrene block copolymer (SBS), styrene-isoprene-styrene block copolymer (SIS) (e.g., VECTOR 4211 provided by Dexco Polymers LP of Houston, Tex.), styrene-isoprene-butadiene-styrene block copolymer, styrene-ethylenebutylene-styrene block copolymer (SEBS), styrene-ethylene-propylene block copolymer (SEP), styrene-ethylene-propylene-styrene block copolymer (SEPS), styrene-ethylene-ethylene-propylene-styrene block copolymer (SEEPS), or mixtures thereof. Some block copolymers include KRATON® Polymers provided by KRATON Polymers LLC of Houston, Tex. (e.g., Series D polymers (such as SIS or SBS copolymers) or Series G (such as SEBS or SEPS block copolymers)), Dexco Polymers LP of Houston, Tex. (e.g., SBS or SIS block copolymers), and Septon Company of America of Pasadena, Tex. (SEP, SEPS, SEBS, or SEEPS block copolymers).

The total amount of the optional nonolefin-based elastomeric polymer can be, relative to the layer weight, about 1 wt %, about 2 wt %, about 3 wt %, about 5 wt %, about 7 wt %, about 10 wt %, about 20 wt %, about 30 wt %, or about 40 wt %. In some instances, total amount of the optional nonolefin-based elastomeric polymer can be at least about 1 wt %, at least about 3 wt %, at least about 5 wt %, at least about 10 wt %, or at least about 20 wt %. The total amount of the optional nonolefin-based elastomeric polymer can be no more than about 40 wt %, no more than about 30 wt %, or no more than about 20 wt %.

The elastomeric film can optionally comprise other components that, in some instances, modify the film properties, aid in the processing of the film, or modify the appearance of the film. Viscosity-reducing polymers and plasticizers can be added as processing aids. High-density polyethylene can be added to help prevent age-related degradation of the other polymers. Other additives such as pigments, dyes, antioxidants, antistatic agents, slip agents, foaming agents, heat stabilizers, light stabilizers, inorganic fillers, organic fillers or combinations thereof can be added. The amounts of these components relative to the layer weight can be about 0.1 wt %, about 0.5 wt %, about 1 wt %, about 2 wt %, about 5 wt %, about 7 wt %, or about 10 wt %.

Any film-forming process can be used to prepare the elastomeric film. For example, any blending process, such as melt blending, can be used. Also, any extrusion process, such as cast extrusion or blown-film extrusion can be used to form the film. If the elastomeric film is a multilayer film, the film can be formed by a coextrusion process.

In some applications, the addition of certain components (e.g., the draw down polymer) to a layer of the elastomeric film confers processing properties that allow extrusion at line speeds of about 175 fpm (feet per minute), about 200 fpm, about 210 fpm, about 225 fpm, about 250 fpm, about 275 fpm, about 300 fpm, about 325 fpm, about 350 fpm, about 400 fpm, about 450 fpm, about 500 fpm, about 750 fpm, about 1000 fpm, about 1500 fpm, about 2000 fpm, about 2500 fpm, about 3000 fpm, or about 5000 fpm. The extrusion line speed can be, for example, greater than about 160 fpm, at least about 175 fpm, at least about 200 fpm, at least about 210 fpm, or at least about 300 fpm. The extrusion line speed can be no more than about 5000 fpm, no more than about 3000 fpm, or nor more than about 2000 fpm. In some embodiments, addition of an effective amount of one or more draw down polymers can provide the aforementioned extrusion line speeds.

The basis weight of the elastomeric film (e.g., a monolayer film) can be no more than about 25 gsm and can be, for example, about 0.1 gsm, about 0.25 gsm, about 0.5 gsm, about 0.75 gsm, about 1 gsm, about 2 gsm, about 3 gsm, about 4 gsm, about 5 gsm, about 6 gsm, about 7 gsm, about 8 gsm, about 9 gsm, about 10 gsm, about 11 gsm, about 12 gsm, about 13 gsm, about 14 gsm, about 15 gsm, about 16 gsm, about 17 gsm, about 18 gsm, about 19 gsm, about 20 gsm, about 21 gsm, about 22 gsm, about 23 gsm, about 24 gsm, or about 25 gsm. In some instances, the basis weight is at least about 0.1 gsm, at least about 0.5 gsm, or at least about 1 gsm. The basis weight can be no more than about 25 gsm, no more than about 20 gsm, no more than about 15 gsm, or no more than about 10 gsm. In some embodiments, the basis weight of from about 1 gsm to about 10 gsm. In some embodiments, addition of an effective amount of one or more draw down polymers can provide the aforementioned basis weights, including, for example, no more than about 25 gsm, no more than about 20 gsm, no more than about 15 gsm, or no more than about 10 gsm.

The permanent set of the elastomeric film after recovery from being stretched to 100% of its original length can be no more than about 15% and can be, for example, about 0.5%, about 1%, about 2%, about 3%, about 4%, about 5%, about 6%, about 7%, about 8%, about 9%, about 10%, about 11%, about 12%, about 13%, about 14%, or about 15%. The permanent set of the elastomeric film after recovery from being stretched to 100% of its original length can be at least about 0.5%, at least about 1%, or at least about 2%. The permanent set of the elastomeric film after recovery from being stretched to 100% of its original length can be no more than about 14%, no more than about 10%, or no more than about 7%. In some instances, the aforementioned permanent set is for films prior to activation, and in other instances the aforementioned permanent set is for films after activation. In some embodiments, addition of an effective amount of elastomeric polymer (i.e., olefin-based elastomeric polymer, nonolefin-based elastomeric polymer, or combinations thereof) can provide the aforementioned permanent set, including, for example, no more than about 15%, no more than about 10%, or no more than about 7%.

In some embodiments, the elastomeric film layers comprise polymers that are inherently sticky or tacky. When such elastomeric films are extruded and wound into a roll, the film can sometimes stick to itself or "block," sometimes becoming difficult or impossible to unwind. Blocking can become more pronounced as the film is aged or stored in a warm environment, such as inside a storage warehouse. This blocking problem can be addressed in a number of ways, if desired. For example, antiblocking agents, such as powdered inorganic materials (e.g., silica or talc) can be incorporated within layers of the film. Antiblocking agents can also be dusted onto the outer surfaces of extruded film as the film is being formed. The elastomeric film can also be surface-coated with materials that are not sticky, such as a nonblocking polymer, a brittle nonblocking polymer, a surface coating such as a lacquer or ink, or other such coatings.

In a further embodiment of the present invention, the elastomeric film can be one or more layers of a multilayer film. In some multilayer embodiments, the elastomeric film includes two or more layers with (1) a first or polyolefin-based layer which comprises one or more olefin-based elastomeric polymers blended with one or more draw down polymers, as discussed above (e.g., including an optional additional elastomeric polymer that is not an olefin-based elastomeric polymer) and (2) a second layer that comprises (a) one or more elastomeric polymers blended with (b) one or more draw down polymers. The elastomeric polymers in the second layer can be can be olefin-based elastomeric polymers, nonolefin based elastomeric polymers, or combinations thereof. The one or more draw down polymers of the first layer can be the same or different as the one or more draw down polymers of the second layer.

In two layer embodiments of the multilayer film, the polyolefin-based layer is sometimes referred to as a "skin" layer, a "surface" layer, or a "capping" layer. And the second layer is sometimes referred to as a "core" layer or a "central" layer. The two layer film can be a coextruded multilayer film.

In some embodiments of a three layer film, the film can be a coextruded multilayer film with an ABC-type construction. In the ABC-type construction, the A layer and the C layer can be the same or different composition. The A layer and the C layer form the outer layers of the film, which are sometimes referred to as the "skin," "surface," or "capping" layers. The B layer, that is also referred to as the "core" or "central" layer, is the layer that comprises one or more elastomeric polymers—the elastomeric polymer can be an olefin-based elastomeric polymer, a nonolefin elastomeric polymer, or combinations thereof. Where the A layer and the C layer are the same composition, this provides an ABA-type construction.

In some instances, the polyolefin-based layer(s) (e.g., the skin layer(s)) can improve the processability of the elastomeric film, even when the second layer (e.g., the core layer) comprises a less-processable polymer (e.g., a styrene block copolymer). Also, olefin-based elastomeric polymers in the skin layer of the film can provide a greater affinity for an olefin-based substrate (e.g., polyolefin fabric) bonded to the surface of the film in a laminate. This greater affinity can improve the overall bond between the film surface and the substrate (e.g., fabric fibers).

The one or more elastomeric polymers in the second layer can be the same as or different from the olefin-based elastomeric polymers of the polyolefin-based layer, can be the same as or different from the optional additional elastomeric polymer of the polyolefin-based layer, or can be combinations thereof.

The total amount of the elastomeric polymer in the second layer can be, relative to the layer weight, about 10 wt %, about 20 wt %, about 30 wt %, about 40 wt %, about 50 wt %, about 60 wt %, about 70 wt %, about 80 wt %, or about 90 wt %. In some instances, total amount of the elastomeric polymer can be at least about 10 wt %, at least about 20 wt %, at least about 50 wt %, at least about 60 wt %, or at least about 70 wt %, least about 80 wt %, or at least about 90 wt %. The total amount of the elastomeric polymer can be no more than about 40 wt %, no more than about 50 wt %, no more than about 60 wt %, no more than about 70 wt %, no more than about 80 wt %, or no more than about 90 wt %.

The polyolefin-based layer (e.g., as a skin layer) can provide improved thermal stability and processability when coextruded with another layer (e.g., a core layer comprising SBC's) to form a multilayer. For example, the presence of the polyolefin-based layer can provide extrusion of very thin elastomeric films with little or no draw resonance, basis weight fluctuations, or web instability.

The draw down polymer in the second layer can be chosen from the draw down polymers as described above and as applied to the polyolefin-based layer. The draw down polymer of the second layer can be the same or different from the draw down polymer of the polyolefin-based layer and can have or confer some or all of the same advantages as the draw down polymer of the polyolefin-based layer. The identity and amount of draw down polymer in the second layer can depend on the other components in the second layer (e.g., the identity of the polymer(s) in the second layer), other components/layers of the film or, if applicable, components of the laminate that comprises the film. The total amount of draw down polymer (i.e., the combined amount of the one or more draw down polymer(s)) in the second layer can be about 5%, about 10 wt %, about 15 wt %, about 20 wt %, about 25 wt %, about 30 wt %, about 35 wt %, or about 45 wt %. The wt % is relative to the layer weight of the second layer (i.e., total weight of draw down polymer(s) divided by the total weight of the layer). In some instances the total amount of the draw down polymer in the second layer is at least about 5 wt %, at least about 10 wt %, or at least about 15 wt %. The total amount of draw down polymer in the second layer can be no more than about 20 wt %, no more than about 30 wt %, no more than about 35 wt %, or no more than about 45 wt %.

The multilayer elastomeric film can have a basis weight of no more than about 40 gsm and can be, for example, about 0.1 gsm, about 0.25 gsm, about 0.5 gsm, about 0.75 gsm, about 1 gsm, about 2 gsm, about 3 gsm, about 4 gsm, about 5 gsm, about 6 gsm, about 7 gsm, about 8 gsm, about 9 gsm, about 10 gsm, about 11 gsm, about 12 gsm, about 13 gsm, about 14 gsm, about 15 gsm, about 16 gsm, about 17 gsm, about 18 gsm, about 19 gsm, about 20 gsm, about 21 gsm, about 22 gsm, about 23 gsm, about 24 gsm, about 25 gsm, about 30 gsm, about 35 gsm, about 36 gsm, about 37 gsm, about 38 gsm, about 39 gsm, or about 40 gsm. In some instances, the basis weight is at least about 0.1 gsm, at least about 0.5 gsm, at least about 1 gsm, or at least about 2 gsm. The basis weight can be no more than about 39 gsm, no more than about 35 gsm, no more than about 30 gsm, or no more than about 25 gsm. In some embodiments, addition of an effective amount of one or more draw down polymers to one or more layers can provide the aforementioned basis weights, including, for example, no more than about 40 gsm, no more than about 35 gsm, no more than about 30 gsm, or no more than about 25 gsm.

The permanent set of the multilayer elastomeric film after recovery from being stretched to 100% of its original length of the multilayer elastomeric film can be no more than about 15% and can be, for example, about 0.5%, about 1%, about 2%, about 3%, about 4%, about 5%, about 6%, about 7%, about 8%, about 9%, about 10%, about 11%, about 12%, about 13%, about 14%, or about 15%. The permanent set of the multilayer elastomeric film after recovery from being stretched to 100% of its original length can be at least about 0.5%, at least about 1%, or at least about 2%. The permanent set of the multilayer elastomeric film after recovery from being stretched to 100% of its original length can be no more than about 14%, no more than about 10%, or no more than about 7%. In some instances, the aforementioned permanent set is for multilayer elastomeric films prior to activation, and in other instances the aforementioned permanent set is for multilayer elastomeric films after activation. In some embodiments, addition of an effective amount of elastomeric polymer (i.e., olefin-based elastomeric polymer, nonolefin-based elastomeric polymer, or combinations thereof) to one or more layers can provide the aforementioned permanent set, including, for example, no more than about 15%, no more than about 10%, or no more than about 7%.

The multilayer elastomeric film can, in some embodiments, be made at extrusion line speeds as discussed above for the monolayer elastomeric film. The compositions of the layers can confer processing properties that allow extrusion at line speeds described herein.

One or more layers of the elastomeric film can optionally comprise other components that, in some instances, modify the film properties, aid in the processing of the film, or modify the appearance of the film. Viscosity-reducing polymers and plasticizers can be added as processing aids. High-density polyethylene can be added to help prevent age-related degradation of the other polymers. Other additives such as pigments, dyes, antioxidants, antistatic agents, slip agents, foaming agents, heat stabilizers, light stabilizers, inorganic fillers, organic fillers or combinations thereof can be added. The amounts of these components relative to the layer weight can be about 0.1 wt %, about 0.5 wt %, about 1 wt %, about 2 wt %, about 5 wt %, about 7 wt %, or about 10 wt %. These additives can be present in one, several, or all layers of a multilayer elastomeric film.

In some embodiments, as desired, the elastomeric multilayer film can include antiblocking agents or other methods/components to address blocking problems associate with layers having polymers that are inherently sticky or tacky, as discussed in more detail above.

As discussed above, any suitable blending method can be used to blend the components of the layers together. Also, any extrusion process, such as cast extrusion or blown-film extrusion can be used to form the multilayer elastomeric film.

By extruding films comprising olefin-based elastomeric polymers or, alternatively, skins comprising olefin-based elastomeric polymers, the processability of the elastomeric film can be improved. And the problems sometimes associated with low basis weight films (e.g., fluctuating basis weights, draw resonance, web tear-offs, etc.) can be reduced or eliminated. The multilayer films described herein can be easier to manufacture when the skin layer(s) comprise(s) olefin-based elastomeric polymers, even when there is a high concentration of elastomeric polymers (e.g., SBCs) in the core layer.

Figure 1:
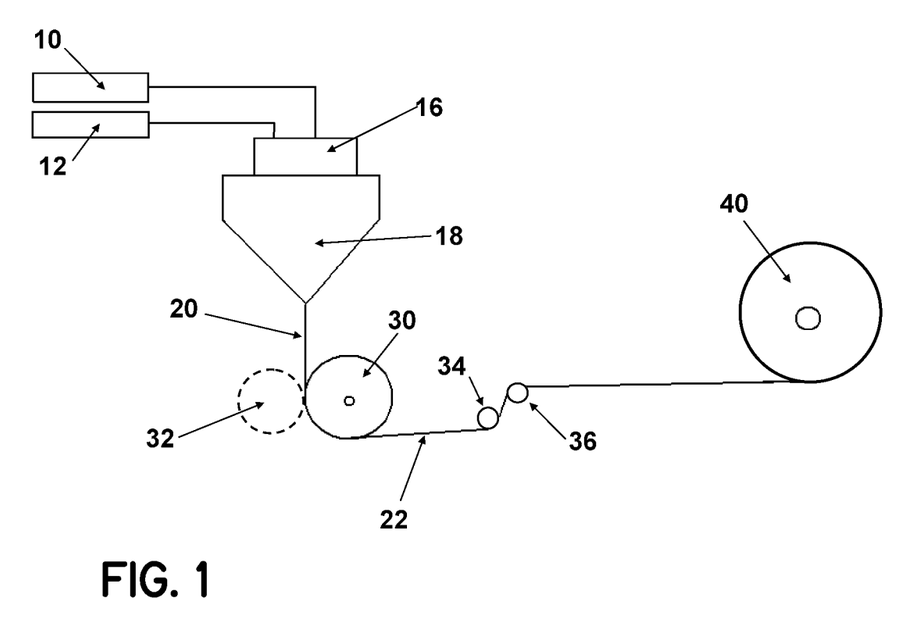
FIG. 1 is a schematic of a typical cast coextrusion process.

FIG. 1 illustrates a schematic of a cast coextrusion film process for an ABA-type three layer multilayer film. A polymer composition for the elastomeric film skin layer A is melted in a conventional screw extruder 10. Similarly, a polymer composition for the elastomeric film core layer B is melted in a conventional screw extruder 12. The molten polymer compositions are then transferred from the extruders to the feed block 16 and the molten polymer layers A and B are then coextruded from the extrusion die 18 to form a molten multilayer polymer web 20. The molten polymer web 20 is extruded onto a cast roll 30 where the web is rapidly cooled to form the film 22. The cast roll 30 may be a smooth roll that makes a smooth film, or an embossing roll which embosses a pattern onto the surface of the film. An optional backing roll 32 can assist the cast roll 30 in forming the film 22. The film 22 may then pass over optional equipment such as idler rolls 34 and 36, which facilitate the transfer of the film from the cast extrusion section to winder 40 where it is wound and stored to await further processing. This process can be modified to make an elastomeric film that is a monolayer elastomeric film.

In some embodiments, the extrusion is performed at line speeds of about 175 fpm (feet per minute), about 200 fpm, about 210 fpm, about 225 fpm, about 250 fpm, about 275 fpm, about 300 fpm, about 325 fpm, about 350 fpm, about 400 fpm, about 450 fpm, about 500 fpm, about 750 fpm, about 1000 fpm, about 1500 fpm, about 2000 fpm, about 2500 fpm, about 3000 fpm, or about 5000 fpm. The extrusion line speed can be, for example, greater than about 160 fpm, at least at about 165 fpm, at least about 175 fpm, at least about 200 fpm, at least about 210 fpm, or at least about 300 fpm. The extrusion line speed can be no more than about 5000 fpm, no more than about 3000 fpm, or nor more than about 2000 fpm.

Additional processing steps can be performed on the elastomeric film, such as activating, aperturing, printing, slitting, laminating additional layers to the film, and other such processes.

For example, the elastomeric film may be activated by stretching means. Machine-direction orientation (MDO) can be used to activate elastomeric films in the machine direction, while tentering can activate films in the cross direction. Incremental stretching rollers can be used to activate films in the machine direction, cross direction, at an angle, or any combination thereof. In some embodiments, the depth of engagement used for incremental stretching is about 0.05 inches, about 0.10 inches, about 0.15 inches, about 0.20 inches, or about 0.25 inches. The depth of engagement can be, for example, at least about 0.05 inches or at least about 0.10 inches. The depth of engagement can be, for example, no more than about 0.10 inches, no more than about 0.18 inches, or no more than about 0.25 inches.

The elastomeric films described herein can also be used to form a laminate. Such a laminate includes one or more substrate layers and the elastomeric film (e.g., monolayers or multilayers). The substrate layer may be an extensible material including but not limited to another polymer film, fabric, nonwoven fabric, woven fabric, knitted fabric, scrim, or netting. The elastomeric film can be bonded to substrate layers on one or both sides.

When two or more substrate layers are used to make the laminate, the substrate layers can be the same or different extensible material. The composition of the substrate layers can be the same or different, even when the same extensible material is used (e.g., two nonwoven layers where one nonwoven layer is made from polyolefin and the other nonwoven layer is made from polyester).

The substrate layer (e.g., nonwoven fabrics) can have a basis weight of about 3 gsm, about 4 gsm, about 5 gsm, about 7 gsm, about 9 gsm, about 10 gsm, about 15 gsm, about 20 gsm, about 25 gsm, about 30 gsm, about 40 gsm, about 50 gsm, about 75 gsm, about 100 gsm, about 150 gsm, or about 200 gsm. The basis weight of the substrate layer (e.g., nonwoven fabrics) can be at least about 3 gsm, at least about 5 gsm, or at least about 10 gsm. The basis weight of the substrate layer can be no more than about 10 gsm, no more than about 20 gsm, no more than about 30 gsm, no more than about 50 gsm, no more than about 75 gsm, no more than about 100 gsm, or no more than about 200 gsm. If two substrate layers are used, one layer can have a basis weight that is the same or different from the other.

In some embodiments, the substrate layer is a nonwoven fabric. For example, the substrate layer can be spunbond nonwoven webs, carded nonwoven webs (e.g., thermally bonded, adhesively bonded, or spunlaced), meltblown nonwoven webs, spunlaced nonwoven webs, spunbond meltblown spunbond nonwoven webs, spunbond meltblown meltblown spunbond nonwoven webs, unbonded nonwoven webs, electrospun nonwoven webs, flashspun nonwoven webs (e.g., TYVEK™ by DuPont), or combinations thereof. These fabrics can comprise fibers of polyolefins such as polypropylene or polyethylene, polyesters, polyamides, polyurethanes, elastomers, rayon, cellulose, copolymers thereof, or blends thereof or mixtures thereof. The nonwoven fabrics can also comprise fibers that are homogenous structures or comprise bicomponent structures such as sheath/core, side-by-side, islands-in-the-sea, and other bicomponent configurations. For a detailed description of some nonwovens, see "Nonwoven Fabric Primer and Reference Sampler" by E. A. Vaughn, Association of the Nonwoven Fabrics Industry, 3d Edition (1992). Such nonwoven fabrics can have a basis weight of at least about 3 gsm, at least about 5 gsm, at least about 10 gsm, no more than about 30 gsm, no more than about 75 gsm, no more than about 100 gsm, or no more than about 150 gsm.

The nonwoven fabrics can include fibers or can be made from fibers that have a cross section perpendicular to the fiber longitudinal axis that is substantially non-circular. Substantially non-circular means that the ratio of the longest axis of the cross section to the shortest axis of the cross section is at least about 1.1. The ratio of the longest axis of the cross section to the shortest axis of the cross section can be about 1.1, about 1.2, about 1.5, about 2.0, about 3.0, about 6.0, about 10.0, or about 15.0. In some embodiments, this ratio can be at least about 1.2, at least about 1.5, or at least about 2.0. These ratios can be, for example, no more than about 3.0, no more than about 6.0, no more than about 10.0, or no more than about 15.0.

The shape of the cross section perpendicular to the fiber longitudinal axis of the substantially non-circular fibers can be rectangular (e.g., with rounded corners) which are also referred to as "flat" fibers, trilobal, or oblong (e.g., oval) in the cross section. These substantially non-circular fibers can provide more surface area to bond to the elastomeric film than nonwoven fabrics with fibers that are circular in cross section. Such an increase in surface area can increase the bond strength between the elastomeric film and fibers.

Bond strength between the elastomeric film and the substrate layers of the laminate can be measured by any number of methods, including, for example, ASTM D-1876. In some embodiments, optimum bond strength is a balance between bond strength that is too low (e.g., that can lead to delamination of the film from the substrate) and bond strength that is too high (e.g., that can lead to inelastic behavior of the laminate, even when activated). Bonding between the layers can be achieved by any method, including, but not limited to, adhesive bonding, extrusion lamination, thermal bonding, ultrasonic bonding, calendering, point bonding, laser bonding, and combinations thereof. The bonding strength can depend on the bonding method and variations within a given bonding method. For example, for layers bonded by an adhesive, the choice of adhesive and the amount of adhesive applied to bond the layers can be adjusted to achieve the desired bond strength.

Bonding can also occur between the substrate layer (e.g., nonwoven) and the elastomeric film during extrusion by heating the film to be molten; this molten film is pressed into the substrate layer to embed the substrate into the film to create bonding. In some instances, this bonding can be enhanced if the chemical composition of the elastomeric film has a chemical affinity for the chemical composition of the substrate layer. Of course, if the elastomeric film is a multilayer film, chemical affinity relative to the substrate layer relates to the layer of the multilayer film that is in contact with the substrate. Similarly, if the substrate is a multilayer substrate or a bicomponent substrate, chemical affinity relative to the film relates to the substrate component that is in contact with the film.

In some embodiments of the process of making the laminate using extrusion with heat, the temperature of the extruded molten elastomeric web can be controlled. For example, when the extruded film is of thin gauge, the extruded web has less mass to retain heat during the extrusion process. Less mass can result in an extruded molten polymer web that can solidify rapidly. An extruded polymer film that solidifies too rapidly can sometimes result in weaker bond strength because less embedding of the substrate in the extruded elastomeric film can occur. In some instances, the bond strength is further decreased when the extruded polymer does not have great chemical affinity for the materials that comprise the substrate.

In some embodiments, film layers comprising SBC do not have strong natural chemical affinity for the polyolefinic substrate materials. To maintain bonding in these instances, sheets of films comprising SBC and substrates with fibers sometimes rely on mechanical bonding forces, such as those achieved by embedding the substrate fibers into the surface of the film. If the film has solidified before contacting the substrate, the fibers cannot be sufficiently embedded into the solidified surface of the film. Hence, the bond strength between the film and substrate of the laminate can be poor, and the elastomeric material can sometimes delaminate easily. Bond strength can be enhanced by other bonding means, such as application of an adhesive. In other embodiments, bond strength can be enhanced by using a multilayer film that includes one layer with a less compatible polymer (e.g., SBC) and one or more layers with a polymer that is more compatible (e.g., an olefin-based elastomeric polymer).

In other embodiments, laminates having films comprising elastomers that are chemically similar to the substrate composition can have increased bonding strength when the substrate is embedded into the film during extrusion. For example, films comprising polyolefins can have chemical affinity for substrates that comprise polyolefins and can therefore have increased bonding strength. In some instances, the chemical affinity (e.g., when the film and the substrate comprise polyolefins) can provide substantial bonding even if there is little or no mechanical bonding (e.g., from embedded fibers in the film). In some instances, if the film is soft or semi-molten when it contacts the substrate, this can lead to enhanced bonding via mechanical bonding. Of course, other methods of bonding (e.g., adhesive bonding) can be used to increase bonding strength.

In some instances, olefin-based elastomeric films do not solidify as rapidly as SBC-based materials. The extruded olefin-based elastomeric web can be semi-molten and soft when it contacts the nonwoven fibers, which allows the fibers to embed into the surface. Hence, olefin-based elastomeric films, or multilayer elastomeric films with olefin-based elastomeric skins, can form laminates with stronger bond strength and less tendency to delaminate.

In some instances, the chemical affinity of the elastomeric film may be sufficiently high that an acceptable bond strength is obtained, but the laminate may be difficult to activate due to a number of factors that may include, for example, the intimate coupling of the nonwoven substrate and the film which can hinder the activation process. The high chemical affinity of the elastomeric film for the nonwoven can sometimes result in roll blocking and thus can sometimes cause problems in storing, transporting, and unwinding of the laminate. Such roll blocking can be addressed by appropriate measures as described herein or by any appropriate method.

Figure 2:
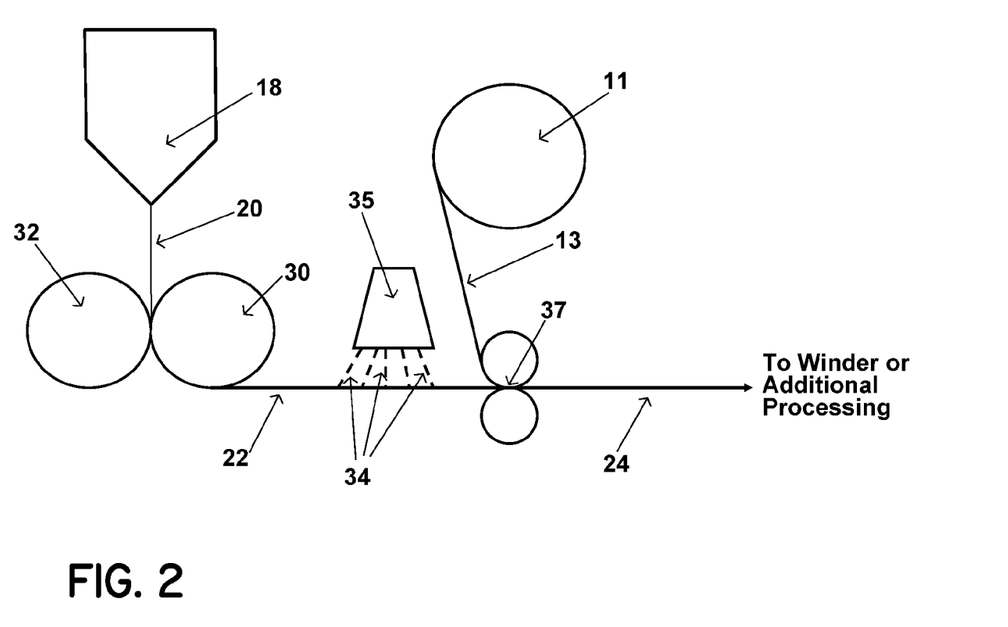
FIG. 2 is a schematic of a typical adhesive lamination process.

One method of forming the laminate is adhesive lamination, illustrated in FIG. 2. The elastomeric film 20 is melt-extruded from a film-forming die 18 and drops to the nip between the illustrated metal roll 30 and backing roll 32. The metal roll 30 may be chilled to rapidly cool the molten film. The metal roll may also be engraved with an embossing pattern if such a pattern is desired on the resulting film. After the extruded film 22 has cooled and solidified, it passes to an adhesive bonding station, where adhesive 34 is applied by means such as a spray unit 35 onto the film. Alternatively, the spray unit 35 may spray adhesive onto the incoming fabric 13. The fabric 13 is unwound from roll 11 and introduced into a nip 37 that presses the elastomeric film 22 and the fabric 13 to bond them together. The laminate 24 may now be wound into a roll or go on for further processing.

Figure 3:
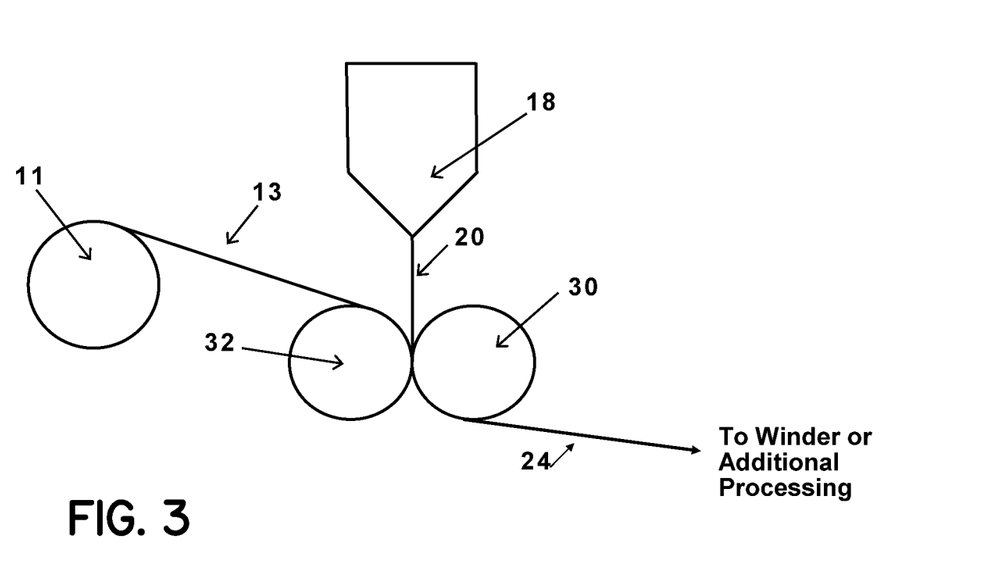
FIG. 3 is a schematic of a typical extrusion coating process.

In another embodiment, an extrusion coating process is used to form the laminate. FIG. 3 illustrates an extrusion coating process. A film 20 is melt-extruded through a film-forming die 18 and drops to the nip between the illustrated metal roll 30 and backing roll 32. The metal roll may be chilled to rapidly cool the molten polymer film. The metal roll 30 may also be engraved with an embossing pattern if such a pattern is desired on the resulting film. The fabric 13 of the laminate is unwound from roll 11 and introduced into the nip between the metal and rubber rolls as well. The extruded film 20 and fabric 13 are pressed together at the nip to bond them together. The laminate 24 may now be wound into a roll or go on for further processing.

Additional processing steps such as activating the elastomeric laminate, aperturing the laminate, printing the laminate, slitting the laminate, laminating additional layers to the laminate, and other such processes can be added to the process.

For another example of additional processing, the laminate can be activated by stretching means. Machine-direction orientation (MDO) can be used to activate laminate in the machine direction, while tentering can activate laminates in the cross direction. Incremental stretching rollers can be used to activate laminates in the machine direction, cross direction, at an angle, or any combination thereof. In some embodiments, the depth of engagement used for incremental stretching is about 0.05 inches, about 0.10 inches, about 0.15 inches, about 0.20 inches, or about 0.25 inches. The depth of engagement can be, for example, at least about 0.05 inches or at least about 0.10 inches. The depth of engagement can be, for example, no more than about 0.10 inches, no more than about 0.18 inches, or no more than about 0.25 inches.

Laminates of elastomeric films and fabrics are particularly suited to activation by incremental stretching. As disclosed in the commonly-assigned U.S. Pat. No. 5,422,172 ("Wu '172"), which is incorporated by reference, laminates of the sort made here can be activated by incremental stretching using the incremental stretching rollers described therein.

EXAMPLES

The following examples are presented to illustrate embodiments of the present invention. These examples are not intended to limit the invention in any way.

Example 1

Elastomeric laminates of the present invention were prepared and tested. The laminates comprised a monolayer elastomeric film and two layers of nonwoven fabric. The monolayer elastomeric films comprised 80% VISTAMAXX™ 6102 polyolefinic elastomer, from ExxonMobil Chemical, 15% ELITE™ 5800 linear low density polyethylene from The Dow Chemical Company, and 5% white masterbatch concentrate (Schulman 8500) from Schulman Corporation. The elastomeric film monolayers were extruded on a cast-extrusion line. Films with target basis weights of less than 20 gsm, and as low as 14 gsm, were extruded with little or no draw resonance, with no web breakage, and with basis weight fluctuation of less than 20%. These films were extrusion laminated to two layers of 8 gsm spunbond-meltblown-meltblown-spunbond (SMMS) polypropylene nonwoven fabric made by Fibertex Nonwovens A/S of Aalborg, Denmark. The laminates were then activated by incremental stretching at a depth of engagement of 0.100 inches for the intermeshing rolls. The thin elastomeric film laminates showed good stretch and recovery characteristics, and the laminates were resistant to pinholes and tearing.

Example 2

Elastomeric laminates of the present invention were prepared and tested. The laminates comprised two layers of nonwoven fabric and a multilayer ABA elastomeric film, where the ABA layers were about 25%/50%/25% of the overall multilayer film composition. The A (skin) layers comprised 75% VISTAMAXX™ 6102 polyolefinic elastomer, 15% ELITE™ 5800 linear low density polyethylene, 5% INSPIRE™ D118.01 homopolymer polypropylene from The Dow Chemical Company, and 5% ALATHON® m6060 high-density polyethylene, from Equistar Chemicals. The B (core) layers comprised 75% VECTOR™ 4211A styrene-isoprene-styrene (SIS) block copolymer (from Dexco Polymer LP of Houston Tex.), 15% ELITE™ 5800 linear low density polyethylene, 5% INSPIRE™ D118.01 homopolymer polypropylene, and 5% white masterbatch concentrate (Schulman 8500) from Schulman Corporation. The multilayer elastomeric films were extruded on a cast-extrusion line. Films with target basis weights of less than 20 gsm, and as low as 10 gsm, were extruded with little or no draw resonance, with no web breakage, and with basis weight fluctuation of less than 20%. This film was extrusion laminated to two layers of 10 gsm flat-fiber bicomponent PE/PP nonwoven fabric (SPUN-BONDED BICO 10 GSM with bilobal 'Papillon' Filaments) from ALBIS Nonwoven Fabrics of Aschersleben, Germany. The laminates were then activated by incremental stretching at a depth of engagement of 0.100 inches for the intermeshing rolls. The thin elastomeric film laminates showed good stretch and recovery characteristics, and the laminates were resistant to pinholes and tearing.

Example 3

Two SMMS nonwoven (spunbond-meltblown-meltblown-spunbond) layers made by Fibertex Nonwovens A/S of Aalborg, Denmark with a basis weight of 10 gsm each were extrusion laminated to a monolayer elastomeric film on both surfaces. The elastomeric film comprised 78% VISTAMAXX™ 6102 from ExxonMobil Company, 15% linear low density polyethylene (LLDPE) (ELITE 5800 from Dow Chemical Company), 5% white master batch (Schulman 8500), and 2% processing aid (LUVOFILM 9679 from Lehmann & Voss & Co. of Hamburg Germany) to make a white elastic film. The film was drawn down to 20 gsm to make the extrusion laminated composite of total basis weight of 40 gsm (i.e., 10 gsm nonwoven+20 gsm film+10 gsm nonwoven).

As a comparison, the same laminate was made except that the film was made without adding LLDPE; the film comprised 93% VISTAMAXX™ 6102, 5% white master batch, and 2% processing aid. This film could only draw down to 46 gsm to make extrusion laminate of total basis weight of 66 gsm (i.e., 10 gsm nonwoven+46 gsm film+10 gsm nonwoven). Attempts to draw down this formulation below 46 gsm caused the web to tear.

Example 4

Table 1 shows properties of films made from an olefin-based elastomeric polymer, ethylene-octene olefin block copolymer (INFUSE™ 9107), with varying amounts of a draw down polymer, LLDPE (ELITE™ 5800).

films can be made that are significantly thinner and that also provide a percent permanent set between 10% and 11.5%.

Example 5

Elastomeric laminates of the present invention were prepared and tested. The laminates comprised one layer of nonwoven fabric and an ABA elastomeric film, where the ABA layers were about 12%/76%/12% of the overall film composition. The A (skin) layers comprised 84% INFUSE™ 9107 polyolefinic elastomer, 15% ELITE™ 5800 linear low density polyethylene, and 1% processing aid (LUVOFILM 9679 from Lehmann & Voss & Co. of Hamburg Germany). The B (core) layers comprised 100% VISTAMAXX™ 6102. The elastomeric films were extruded on a cast-extrusion line. The films had basis weights of 25 gsm. This film was extrusion laminated to one layer of 18 gsm (70/30 core/sheath) bicomponent spunbond, produced at Fiberweb (Washougal, Wash.). Laminates were activated by incremental stretching with CD activation at a depth of engagement of 0.140 inches or 0.160 inches. No pinholes were observed with any of the laminates.

Example 6

Elastomeric laminates of the present invention were prepared and tested. The laminates comprised one layer of nonwoven fabric and an ABA elastomeric film, where the ABA layers were about 12%/76%/12% of the overall film composition. The A (skin) layers comprised 69% INFUSE™ 9107 polyolefinic elastomer, 30% ELITE™ 5800 linear low density polyethylene, and 1% processing aid (LUVOFILM 9679 from Lehmann & Voss & Co. of Hamburg Germany). The B (core) layers comprised 100% VISTAMAXX™ 6102. The elastomeric films were extruded on a cast-extrusion line. The films had basis weights of 25 gsm. This film was extrusion laminated to one layer of 18 gsm (70/30 core/sheath) bicomponent spunbond, produced at Fiberweb (Washougal, Wash.). Laminates were activated by incremental stretching with CD activation at a depth of engagement of 0.140 inches or 0.160 inches. No pinholes were observed with any of the laminates.

Example 7

Elastomeric laminates revealed the use of the skin layers as tie layers to achieve good bond strength for a variety of

TABLE 1

|  |  | Sample 4-A | Sample 4-B | Sample 4-C |
|---|---|---|---|---|
| Formulation | INFUSE ™ 9107 (%) | 92 | 82 | 77 |
|  | ELITE ™ 5800 (%) | 0 | 10 | 15 |
|  | Processing aid (LUVOFILM 9679) (%) | 1 | 1 | 1 |
|  | White Master Batch (Schulman 8500) (%) | 7 | 7 | 7 |

|  | Line Speed (fpm) | Basis weight (gsm) | % permanent set after 100% strain | Basis weight (gsm) | % permanent set after 100% strain | Basis weight (gsm) | % permanent set after 100% strain |
|---|---|---|---|---|---|---|---|
| Draw down | 110 | 20 | 7.3 | n.d. | n.d. | 20 | 8.4 |
| performance | 130 | n.d. | n.d. | 18 | 7.4 | nd | n.d. |
| of the | 160 | 15 | 8.8 | n.d. | n.d. | 15 | 8.8 |
| formulations | 210 | Web Tears | Web Tears | 10 | 10.4 | n.d. | n.d. |
| and their | 300 | Web Tears | Web Tears | n.d. | n.d. | 6 | 11.4 |
| elasticity | 350 | Web Tears | Web Tears | 5 | 11.2 | n.d. | n.d. | n.d.—not determined

Sample 4-A shows that the web tears off during extrusion when produced at line speeds of 210 fpm and higher. At line speeds of 210 fpm and higher, samples 4-B and 4-C show that nonwovens with flat fiber webs, round fiber webs, BICO fibers with mixed PE and PP, or sheath/core of PE/PP. In some instances, the skin layer of the elastomeric film was ethylene-propylene elastomer rich with polypropylene. In some instances, the skin layer of the film included an elastomeric polymer that comprised hard and soft segments of ethylene block polymer. The data showed that using films with skin (e.g., tie) layers of ethylene block polymer in contact with ethylene nonwoven or bico nonwoven can enhance the bond strength. The data also showed that using films with skin (e.g., tie) layers with propylene-rich ethylene-propylene elastomer can bond better to polypropylene nonwovens.

As discussed above in more detail, embodiments of the present invention include elastomeric films with a low basis weight and methods for making the elastomeric films. In some embodiments, the elastomeric film is a monolayer film of a polyolefin-based layer. The elastomeric film can also be a multilayer film having a polyolefin-based layer. The elastomeric film can also be part of a laminate formed with one or more substrates, such as nonwoven fabrics. The choice of components (e.g., draw down polymers, olefin-based elastomeric polymers, and other elastomeric polymers) and component amounts in the layers of the elastomeric film can confer both beneficial film properties and film processing properties. For example, elastomeric films (i.e., monolayer and multilayer) that have a low basis weight and good permanent set can be produced with at high line speeds.

What is claimed is:

1. A laminate comprising:
   (1) an elastomeric film comprising a first surface and a second surface comprising:
      (i) at least one non-styrenic elastomeric polymer selected from the group consisting of an olefin block copolymer, copolymers of polypropylene and polyethylene, and mixtures thereof in an amount of at least about 50% of said film;
      (ii) at least one draw down polymer present in a combined amount of from about 5 wt % to about 25 wt % of said film, said at least one draw down polymer is selected from the group consisting of linear low density polyethylene, high density polyethylene, homopolymer polypropylene, and mixtures thereof,
      wherein said elastomeric film has a basis weight of no more than about 25 gsm and said elastomeric film has a permanent set of no more than 14% after recovery from being initially stretched to twice its original size and;
   (2) a first substrate laminated to said first surface to form said laminate.

2. The laminate of claim 1, wherein said first substrate comprises a nonwoven fabric.

3. The laminate of claim 1, wherein said first substrate comprises a nonwoven fabric selected from the group consisting of spunbond nonwoven webs, carded nonwoven webs, meltblown nonwoven webs, spunlaced nonwoven webs, spunbond meltblown spunbond nonwoven webs, spunbond meltblown meltblown spunbond nonwoven webs, unbonded nonwoven webs, and combinations thereof.

4. The laminate of claim 1, wherein said first substrate has a basis weight of from about 3 gsm to about 100 gsm.

5. The laminate of claim 2, wherein the nonwoven fabric comprises fibers with a cross section perpendicular to the fiber longitudinal axis that is rectangular, oblong, trilobal or triangular.

6. The laminate of claim 2, wherein the nonwoven fabric comprises fibers with a cross section perpendicular to the fiber longitudinal axis having a longest axis and a shortest axis and the ratio of the length of the longest axis to the length of the shortest axis is about 1.1 to about 15.0.

7. The laminate of claim 2, wherein said lamination occurs using adhesive bonding, thermal bonding, extrusion lamination, ultrasonic bonding, calendaring or combinations thereof.

8. The laminate of claim 1, wherein said laminate further comprises a second substrate laminated to said second surface.

9. The laminate of claim 8, wherein said first substrate and said second substrate are composed of the same nonwoven fabric material.

10. The laminate of claim 1, wherein said laminate is activated by stretching.

11. The laminate of claim 10, wherein said activation occurs using incremental stretching.

12. The laminate of claim 1 wherein said at least one non-styrenic elastomeric polymer is present in a combined amount of from 70% wt % to 90 wt % of said film.

13. The laminate of claim 1, wherein said draw down polymer is a polyolefin prepared with a single site catalyst.

14. A laminate comprising:
   (1) a multilayer elastomeric film, said film having a first surface and a second surface, comprising:
      (a) a first layer comprising:
         (i) at least one non-styrenic elastomeric polymer e selected from the group consisting of ethylene olefin block copolymers, propylene olefin block copolymers, copolymers of polypropylene and polyethylene and mixtures thereof, in an amount of at least about 50% of said film;
         (ii) at least one draw down polymer present in a combined amount of from about 5 wt % to about 25 wt % of said film, said at least one draw down polymer is selected from the group consisting of linear low density polyethylene, high density polyethylene, homopolymer polypropylene, and mixtures thereof,
      (b) a second layer comprising
         (i) at least one elastomeric polymer and
         (ii) at least one second draw down polymer
      wherein said multilayer elastomeric film has a basis weight of no more than about 40 gsm, and said multilayer elastomeric film has a permanent set of no more than 14% after recovery from being initially stretched to twice its original size, and
   (2) a first substrate laminated to said first surface to form said laminate.

15. The laminate of claim 14, wherein said elastomeric polymer of said second layer is an olefinic elastomeric polymer.

16. The laminate of claim 15, wherein said olefinic elastomeric polymer of said second layer is a non-styrenic elastomeric polymer selected from the group consisting of ethylene olefin block copolymers, propylene olefin block copolymers, ethylene olefin random copolymers, propylene olefin random copolymers, ethylene-propylene random copolymers, and mixtures thereof.

17. The laminate of claim 14, wherein said first substrate comprises a nonwoven fabric.

18. The laminate of claim 17, wherein said nonwoven fabric is selected from the group consisting of spunbond nonwoven webs, carded nonwoven webs, meltblown nonwoven webs, spunlaced nonwoven webs, spunbond meltblown spunbond nonwoven webs, spunbond meltblown meltblown spunbond nonwoven webs, unbonded nonwoven webs, and combinations thereof.

19. The laminate of claim 17, wherein the nonwoven fabric comprises fibers with a cross section perpendicular to the fiber longitudinal axis that is rectangular, oblong, trilobal or triangular.

20. The laminate of claim 17, wherein the nonwoven fabric comprises fibers with a cross section perpendicular to the fiber longitudinal axis having a longest axis and a shortest axis and the ratio of the length of the longest axis to the length of the shortest axis is about 1.1 to about 15.0.

21. The laminate of claim 14, wherein said first substrate has a basis weight of from about 3 gsm to about 100 gsm.

22. The laminate of claim 14, wherein said lamination occurs using adhesive bonding, thermal bonding, extrusion lamination, ultrasonic bonding, calendaring or combinations thereof.

23. The laminate of claim 14, wherein said laminate further comprises a second substrate laminated to said second surface.

24. The laminate of claim 14, wherein said laminate is activated by stretching.

25. The laminate of claim 24, wherein said stretching is incremental stretching.

26. The laminate of claim 14, wherein said draw down polymer is a polyolefin prepared with a single site catalyst.

27. A laminate comprising:
(1) an elastomeric film comprising a first surface and a second surface comprising:
(i) a non-styrenic olefin block copolymer in an amount of at least about 70% of said film;
(ii) at least one draw down polymer present in a combined amount of from about 5 wt % to about 25 wt % of said film, said at least one draw down polymer is selected from the group consisting of linear low density polyethylene, high density polyethylene, homopolymer polypropylene, and mixtures thereof,
wherein said elastomeric film has a basis weight of no more than about 25 gsm and said elastomeric film has a permanent set of no more than 14% after recovery from being initially stretched to twice its original size and;
(2) a first substrate laminated to said first surface to form said laminate.

28. A laminate comprising:
(1) an elastomeric film comprising a first surface and a second surface comprising:
(i) a non-styrenic elastomeric copolymer of polypropylene and polyethylene in an amount of at least about 70% of said film;
(ii) at least one draw down polymer present in a combined amount of from about 5 wt % to about 25 wt % of said film, said at least one draw down polymer is selected from the group consisting of linear low density polyethylene, high density polyethylene, homopolymer polypropylene, and mixtures thereof,
wherein said elastomeric film has a basis weight of no more than about 25 gsm and said elastomeric film has a permanent set of no more than about 14% after recovery from being initially stretched to twice its original size and;
(2) a first substrate laminated to said first surface to form said laminate.

29. The laminate of claim 1, wherein said at least one substrate comprises a nonwoven fabric comprising fibers with a cross section perpendicular to the fiber longitudinal axis that is substantially non-circular.

* * * * *